(12) United States Patent
Wolf et al.

(10) Patent No.: US 6,280,586 B1
(45) Date of Patent: Aug. 28, 2001

(54) MEASURING DEVICE USING BIOLOGICAL CELLS OR CHEMICAL BIOLOGICALLY ACTIVE SUBSTANCES CONTAINED IN AN ANALYTE

(75) Inventors: Bernhard Wolf, Stegen; Ralf Ehret, Merdingen; Ulrich Sieben, Reute; Werner Baumann, Bühl-Altschweier, all of (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 08/930,657
(22) PCT Filed: Mar. 30, 1996
(86) PCT No.: PCT/EP96/01409
§ 371 Date: Oct. 2, 1997
§ 102(e) Date: Oct. 2, 1997
(87) PCT Pub. No.: WO96/31774
PCT Pub. Date: Oct. 10, 1996

(30) Foreign Application Priority Data
Apr. 4, 1995 (DE) .............................. 195 12 117

(51) Int. Cl.$^7$ ..................... G01N 33/543; G01N 27/414; G01N 27/327
(52) U.S. Cl. .................... 204/403; 204/406; 257/253
(58) Field of Search .................. 204/403, 406; 257/253; 435/817

(56) References Cited

U.S. PATENT DOCUMENTS

| | | | |
|---|---|---|---|
| 5,120,421 | * 6/1992 | Glass et al. | 204/406 |
| 5,200,051 | * 4/1993 | Cozzette et al. | 204/403 |
| 5,264,103 | * 11/1993 | Yoshioka et al. | 204/403 |
| 5,278,048 | 1/1994 | Parce . | |
| 5,286,364 | * 2/1994 | Yacynych et al. | 204/418 |
| 5,309,085 | * 5/1994 | Sohn | 204/403 |
| 5,345,213 | * 9/1994 | Semancik et al. | 257/253 |
| 5,466,348 | * 11/1995 | Holm-Kennedy | 204/403 |
| 5,512,492 | * 4/1996 | Herron et al. | 436/518 |
| 5,622,872 | * 4/1997 | Ribi | 204/403 |

FOREIGN PATENT DOCUMENTS

| | | | |
|---|---|---|---|
| 0 128 438 A1 | 12/1984 | (EP) . | |
| 0 402 917 A2 | 12/1990 | (EP) . | |
| 0 545 284 A1 | 6/1993 | (EP) . | |
| 61-218932 | * 9/1986 | (JP) | 257/253 |
| WO 88/09808 | 12/1988 | (WO) . | |
| WO 93/08464 | 4/1993 | (WO) . | |
| WO 93 22678 | 11/1993 | (WO) . | |
| WO 94/29708 | * 12/1994 | (WO) | 204/403 |

OTHER PUBLICATIONS

Kraus et al. "Biosensing with Cellular Systems", Bioscope, 1, pp. 24–33, 1993.*

Klaus Riedel et al., "Microbial Sensors: Fundamentals and Application for Process Control", J. Chem. Tech. Biotechnol. 44, (1989), pp. 85–106.

Isao Karube, "Microbial Sensor", Journal of Biotechnology, 15, (1990), pp. 255–266.

Y.I. Korpan et al., "A Cell Biosensor Specific for Formaldehyde Based on pH–Sensitive Transistors Coupled to Methylotrophic Yeast Cells with Genetically Adjusted Metabolism", Analytical Biochemistry, 215, (1993), pp. 216–222.

* cited by examiner

Primary Examiner—Robert J. Warden, Sr.
Assistant Examiner—Kaj K. Olsen
(74) Attorney, Agent, or Firm—Akin, Gump. Strauss, Hauer & Feld, L.L.P.

(57) ABSTRACT

A measuring device (1) for measuring or investigating physiological parameters using biological cells or chemical and biologically active substances contained in an analyte (2). The measuring device comprises a sensor (4) with an electronic measurement structure (6) located on a substrate (5). Function-specific receptor cells and/or target cells (7) form part of the sensor (4) and are in direct contact with the measurement structure (6). For measurement, the medium under investigation can be brought into contact with the target cells or receptor cells (7). The measuring device (1) is especially compact in its design and facilitates largely feedback-free investigation of biological or chemical components contained in the analyte.

17 Claims, 12 Drawing Sheets

MEASURING DEVICE USING BIOLOGICAL CELLS OR CHEMICAL BIOLOGICALLY ACTIVE SUBSTANCES CONTAINED IN AN ANALYTE

The invention relates to a measuring device for measuring or investigating physiological parameters using biological cells or chemical biologically active substances contained in an analyte. The measuring device includes at least one electrical or electronic sensor having a measurement output connectable to an evaluating device, wherein the sensor has at least one electrical or electronic measurement structure located on a substrate. The measurement structure is connected to function-specific receptor cells and/or target cells serving as biological sensors (discriminator) and together with these cells forms a sensor, such that the cells are an inherent part of the sensor and for measurement of the analyte under investigation can be brought into contact with the receptor cells and/or the target cells on their side facing away from the measurement structure.

BACKGROUND OF THE INVENTION

A measuring device of the type mentioned above is already known from the publication "Kraus et al, BIO-SCOPE 1993, No. 1, Pages 24 to 33". Although this measuring device is field-proven in practice, particularly due to its quick response time and the possibility of carrying out selective measurements in the analyte, it nevertheless presents drawbacks. Thus, the function-preserving immobilization of the receptor cells and/or target cells on the physical component of the sensor is extremely critical. One possibility of bringing the receptor cells or target cells into contact with the measurement structure of the measuring device consists, by way of example, in fixing the receptor cells and/or target cells on the measurement structure in an immobile fashion with a gel. This has the drawback, however, that the receptor cells and/or target cells are prestimulated and by this means supply only a comparatively faint signal upon contact with a substance to be detected. Another possibility of bringing the receptor cells and/or target cells into contact with the measurement structure consists in attaching the receptor cells and/or target cells to the measurement structure by mechanical means, for instance using a micromanipulator. This method is, however, comparatively complex, because the micromanipulator has to be manually positioned on the cells under a microscope. In addition, the size of the measuring device, which as such is very compact, is significantly increased by adding the micromanipulator.

A measuring device is also already known where the cells under investigation are contained in a biological buffer medium and where an auxiliary reagent is added to this buffer medium and, when certain chemical components are present, causes coloration of the buffer medium. Thus, by way of example, a calcium colorant can be contained in the buffer medium for detection of calcium ions. For measurement of a change in color brought about by the substance to be detected, the known measuring device has an optical sensor and a light source for transmitting light through the buffer medium. A drawback of this measuring device is particularly that it is of some size and is therefore not sufficiently versatile in use for certain measurements. In addition, the measurement is not free from reactive effect, since some of the auxiliary reagents required are toxic and influence the cells under investigation or the cellular targets. The high photon densities can also lead to changes in the measurement system.

In addition, sensors on enzymatic basis or with microbial structure are known. However, they permit only a single signal analysis, i.e. these sensors always measure only one analyte. What is more, such sensors are vulnerable, because the measurement of a spurious signal does not permit any dependable analyte recognition.

SUMMARY OF THE INVENTION

The object underlying the invention is therefore to provide a measuring device of the type set forth at the outset, which is compact in size, where the influence upon the medium under investigation by the measuring device is reduced and which, apart from a selective evaluation, also displays a high measuring sensitivity.

This object is accomplished in that provided between the receptor cells and/or target cells and the measurement structure is a structured, microporous interlayer which the target cells and/or receptor cells accept as neighbor for adherence.

Such a sensor, in principle comprising a sensor element on the input side, similar to an electrical discriminator and a transducer composed by the electrical or electronic measurement structure, allows measurements with very high measuring sensitivity. As a result, animal or vegetable cells as a constituent of the sensor, which are spontaneously adherent or were rendered adherent to the measurement structure, permit a highly sensitive, dynamic substance recognition, since the parallel signal processing mechanisms of the cells are utilized as a discriminator unit.

A further advantage is constituted by the fact that cell membrane-bound receptors after loading with an analyte are immediately recycled by the cells and a new receptor is transported to the cell surface. This effect can be optimized in a steered fashion by biotechnological measures (e.g. by transgenic receptors). Compared with conventional and also microbial sensors, sensor structures which are highly dynamic and display high sensitivity through the internal signal amplifying mechanism of the cells are possible.

In the measuring device according to the invention, the sensor hence cooperates with the target cells or receptor cells which are arranged directly on the measurement structure and, upon contact with the analyte or medium under investigation, are influenced by certain substances contained therein. The changes thereby brought about in the target cells or receptor cells are directly measurable by the sensor, so that the electric signal delivered by the sensor allows conclusions to be drawn on the substances and/or cells contained in the analyte. Depending on the special properties of the function-specific receptor cells and/or target cells coupled to the sensor, a wide range of substances can be measured or detected. In this way, for instance, receptor cells can be provided for the detection of opiates, atracin, steroids or oestrogens. By means of special target cells, biological (e.g. toxic), chemical (e.g. heavy metals etc.) and physical (e.g. radiation) components can be detected.

Since the measuring device according to the invention is very small in size, it can be handled particularly well and can also be used at places difficult of access. In addition, only a correspondingly small amount of the medium under investigation is required for the measurement. Since no auxiliary reagents have to be added to the substance under investigation, or more specifically to the analyte, the measuring device operates practically non-reactively. The interlayer provided is in particular a macromolecular porous layer which on the one hand induces adhesion of the cells and on the other hand is proportioned in the pore size so as to be permeable for certain ions, molecules or cell areas. By way of example, an $SiO_2$ layer sputtered or applied to the measurement structure, an $Al_2O_3$ layer or a $Ta_2O_5$ layer can also be provided as the interlayer. By means of the structured interlayer, the electronic measurement structure is conditioned in such a way that the target cells or receptor cells accept the measurement structure as neighbor and become better attached to it. The porosity of the interlayer allows that the ions, molecules or cell areas to be measured of the target cells or receptor cells can reach the electrically active areas of the measurement structure.

It is especially advantageous if a plurality of sensors with measurement structures are arranged, particularly as a sensor array, on a common substrate. Such a sensor array can be manufactured particularly cost-advantageously as an integrated circuit and allows the measurement of a wide range of chemical or biological substances in a most confined space. In this context, there is the possibility that a plurality of sensors with the same measurement structures be arranged, particularly as a sensor array, on a common substrate. By the same token, it is also possible that a plurality of sensors with different measurement structures be arranged, particularly as a sensor array, on a common substrate. Furthermore, a plurality of measurement structures with cells and in addition cell-free measurement structures can be arranged on a common substrate. Cellular sensor structures and cell-free measurement structures supply a parallel data pattern enabling substance- and function-specific sensor performance.

Suitably, the measurement outputs of the sensors arranged on a common substrate are connected to a control and evaluating device, particularly one arranged integrated on the substrate. By way of example, pre-processing of the measured values can be carried out in the integrated control and evaluating device. The electronic evaluating device also permits a substance- and function-specific training of the sensor.

Enhanced versatility of use of the sensors situated on the substrate can be achieved by arranging on the substrate with the sensor array, a multiplexer, an AD/DA converter with sensor control, a microprocessor and an IO unit as a control and evaluating device. The microprocessor can then compensate offset voltages and temperature drifts of the sensors and if necessary also attend to the processing or evaluation of the measured values. The multiplexer in conjunction with the IO unit and the AD/DA converter enables the transfer of measured values concurrently established by a multitude of sensors by way of a data bus or by way of a common data line.

A preferred embodiment of the invention contemplates that at least one stimulating electrode for the receptor cells or target cells is arranged on the substrate exhibiting the measurement structure, within or adjacent to the measurement area. The target cells or receptor cells can then be selectively stimulated by the stimulating electrode and induced to spontaneously release a physiological substance to be detected by the sensor.

It is particularly advantageous if the substrate is a semiconductor substrate and if the measurement structure is provided in the form of at least one field effect transistor, particularly an ISFET, whose gate is exposed for contact with the receptor cells or target cells. In this context, if it does not contain any substances toxic for the cells, the gate can be in direct contact with the target cells or receptor cells. However, between the gate and the target cells or receptor cells there can also be an interlayer provided, for instance an $SiO_2$ layer for a potential measurement with desired transverse sensitivity for pH or, however, also an an aluminum oxide or tantalum pentoxide layer for proton-specific measurements. Furthermore, a solid membrane, for instance a thin glass membrane can also be deposited on the gate.

Another advantageous embodiment contemplates a measurement structure in the form of at least one interdigital capacitor exhibiting electrodes preferably arranged in pairs, for instance in comb or meander structure. The spacing of the comb-type or capacitor electrodes is adapted to the diameter of the target cells or receptor cells, so that the latter can be in contact with differently polarized capacitor electrodes. An interdigital capacitor as measurement structure is suited particularly for the measurement of changes in shape of the target cells or receptor cells, as may be caused for instance in target cells by the presence of heavy metals or in transgenic cells by contact with a certain receptor. In addition, impedance or capacitance changes of the cell membrane can be measured with interdigital capacitors. Antibodies becoming attached to target cells or receptor cells can also be detected by an interdigital structure, since they change the dielectric constant in the region of the interdigital structure. For measurement of capacitance changes, a thin insulating layer is preferably provided between the electrodes of the interdigital capacitor and the target cells or receptor cells.

A plurality of interdigital capacitors preferably varying in size are suitably provided for the measuring device. The individual sensors then have a differing sensitivity, so that the measuring device covers a larger measuring range and enables a higher resolution in the individual measurement areas. The sensitivity of the measuring device can also be enhanced by moving the analyte relative to the target or receptor cells before or during measurement, e.g. by agitating the analyte or by shaking the measuring device.

It is advantageous if an electrochemo-sensitive layer is provided in at least one insulated interspace of the electrodes of the interdigital capacitor. The sensor is then better suited for detecting certain physiological substances, e.g. oxygen or complex gases liberated by the target cells or receptor cells. For this, electroactive substances can be applied in the interspaces or packed in ceramic sponges.

In another embodiment, light guides are provided between the electrodes of the interdigital capacitor and light detectors for reception and detection of the light passing through the respective light guide are arranged in the substrate. The measuring device then provides additional information relating, for instance, to scattered light emitted by the target cells or receptor cells, enabling a conclusion to be drawn on the vitality of the cells. In an advantageous way, a self-test of the measuring device can therefore be carried out with the aid of the light detectors.

Even more accurate control of the target cells or receptor cells in contact with the measurement structures is enabled in that CCD sensors, in particular in the form of a CCD line or CCD array, are integrated in the substrate. By this means, an even higher resolution in the optical measurement is attained, so that in particular it is also possible to monitor morphological changes of some or several cells arranged in certain areas of the measurement structure.

Suitably at least one reference element with a design the same as or similar to that of the measurement structure, particularly a field effect transistor with gate in the case of a field effect transistor as measurement structure, is arranged on the substrate exhibiting the measurement structure, outside the substrate area designated for the measurement. With such reference elements, it is possible to compensate e.g.

temperature drifts or offset voltages of the measurement structures designated for the measurement.

It is advantageous if at least one temperature measuring sensor, particularly a temperature measuring diode, is arranged on the substrate exhibiting the measurement structure. The temperature dependence of the biological activity of the target cells or reference cells can then be taken into account during the measurement and, if necessary, compensated.

One embodiment of the invention contemplates that the receptor cells are arranged in or covered by a gel structure. By means of the gel structure, the cells belonging to the sensor can be made adherent to the measurement structure and thus be brought into direct contact with and immobily connected to the measurement structure of the sensor. The gel structure also acts as a moisture and nutritional reservoir for the target cells or receptor cells, so that they can be kept alive over a longer period. By this means, the measuring device permits uninterrupted on-line signal acquisition over a period of about 10 days for a biological or chemical component contained in the analyte. An advantage of the gel structure also consists in that the mesh size of the gel structure can be adapted to the diameter of the ions, molecules or cell areas to be detected, so that ions, molecules or cell areas having a larger diameter than the mesh size or the corresponding charge profiles can by no means advance to the target cells or receptor cells.

A further development of the invention contemplates that the electrical or electronic measurement structure is part of a wall of a receptacle for the medium under investigation. The medium under investigation can then be brought better into contact with the target cells or receptor cells adherently attached to the sensor surface, because it can be simply filled into the receptacle and then immediately contacts the target cells or receptor cells.

It is especially advantageous if the measurement structure is situated on the bottom of the receptacle and if the side walls are formed by an encapsulation bounding the measurement area of the measurement structure. The sensor is hence incorporated in the wall of the receptacle in such a way that only the measurement area of the measurement structure is exposed, while the electrical connections of the sensor are sealed by the encapsulation from the medium situated in the receptacle.

A preferred embodiment of the invention contemplates that a plurality of measurement structures are arranged preferably side by side. By this means, measurements can be carried out concurrently at different locations of a medium under investigation, so that on the one hand inhomogeneities in the medium under investigation can be established and on the other hand a check on the measurement results is also possible by comparison of the measurement signals of a plurality of measurement structures arranged side by side.

It is advantageous if the electrical contact points and/or the structured interlayers of at least two measurement structures have different specificity. The individual measurement structures by this means enable a selective measurement of different ions, molecules or cell areas. In particular, the separation of a certain constituent of a physiological substance, for instance in certain cell processes, can be selectively measured. $CO$, $CO_2$, $NH_3$, $H_2S$, $CH_4$, $C_2H_5OH$, $O_2$, $NO$, as well as protons, by way of example, are possibilities as separated constituents.

BRIEF DESCRIPTION OF THE DRAWINGS

The invention will be discussed in greater detail below with reference to exemplary embodiments.

In the drawings, heavily schematized in parts.

DETAILED DESCRIPTION OF THE INVENTION

Figure 1:
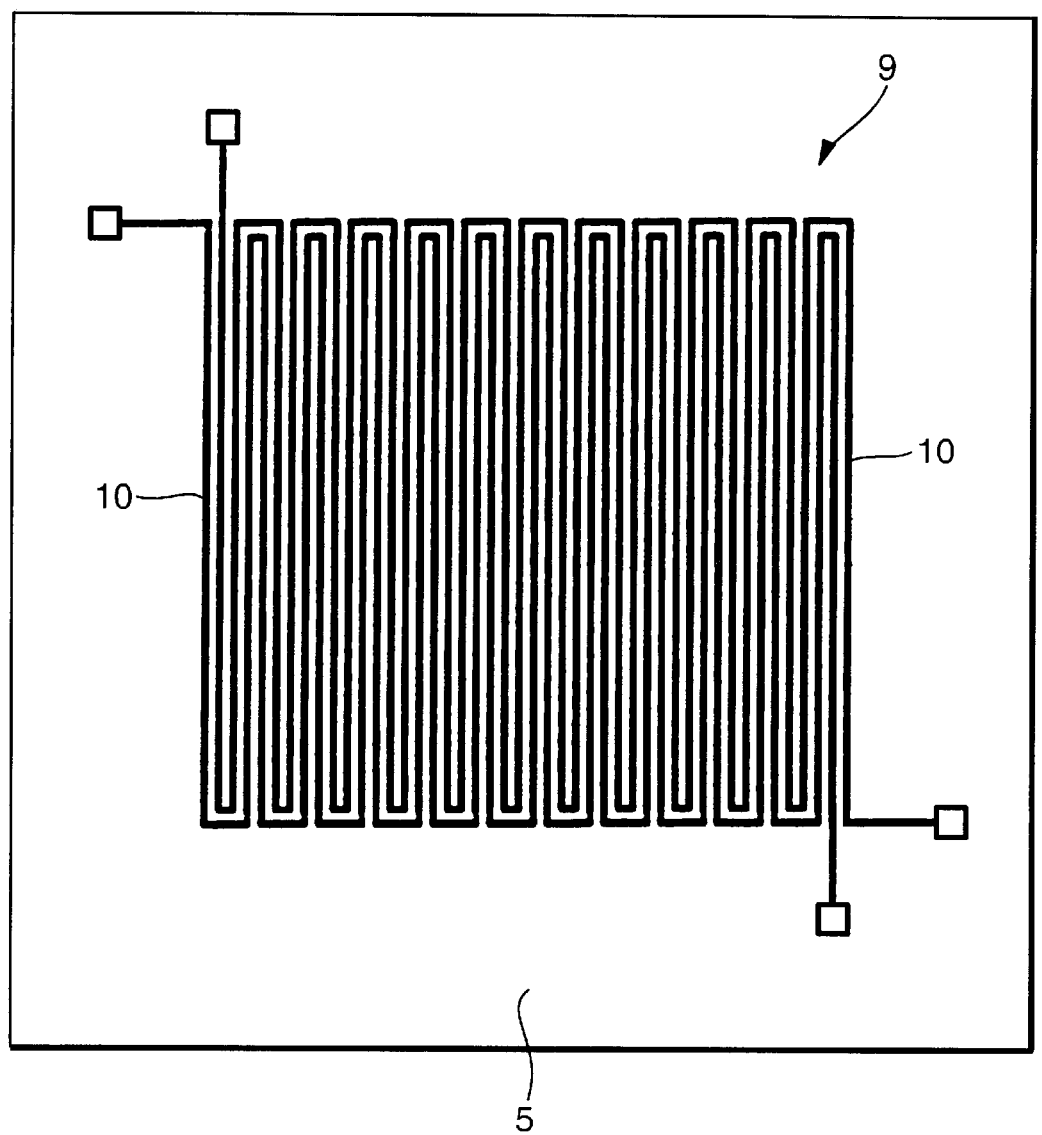
FIG. 1 is an interdigital capacitor which is situated on a substrate and has electrodes extending meander-like in parallel relationship.

A measuring device, generally designated 1, for measuring or investigating physiological parameters using biological cells or chemical components 3 contained in an analyte 2 has a sensor 4 with a measurement structure 6 arranged on a substrate 5 (FIG. 5). The sensor 4 is combined with about 30 receptor cells 7 arranged on and in direct contact with the surface of the measurement structure 6. The receptor cells 7 have receptors 8 for specific chemical or biological components 3. If these components 3 are contained in the analyte 2, they become attached to the receptors 8. The components 3 can be, by way of example, hormones, antibodies, antigens or growth factors. The receptor cells 7 are changed by the coupling of the chemical components 3 and this change can be detected by the measurement structure 6. Thus, by way of example, certain heavy metal ions contained in the analyte 2 bring about changes in shape of the receptor cells 7, resulting in the cell membrane undergoing an impedance change detectable by the measurement structure 6. In the measuring device 1 according to the invention, the sensor 4 hence measures changes of the receptor cells 7, which are caused by the chemical or biological components 3 contained in the analyte 2. For all practical purposes, the sensor concerned here is a bio-electronic sensor in which a biological sensor (receptor cells or target cells) is combined with an electrical or electronic sensor.

Figure 2:
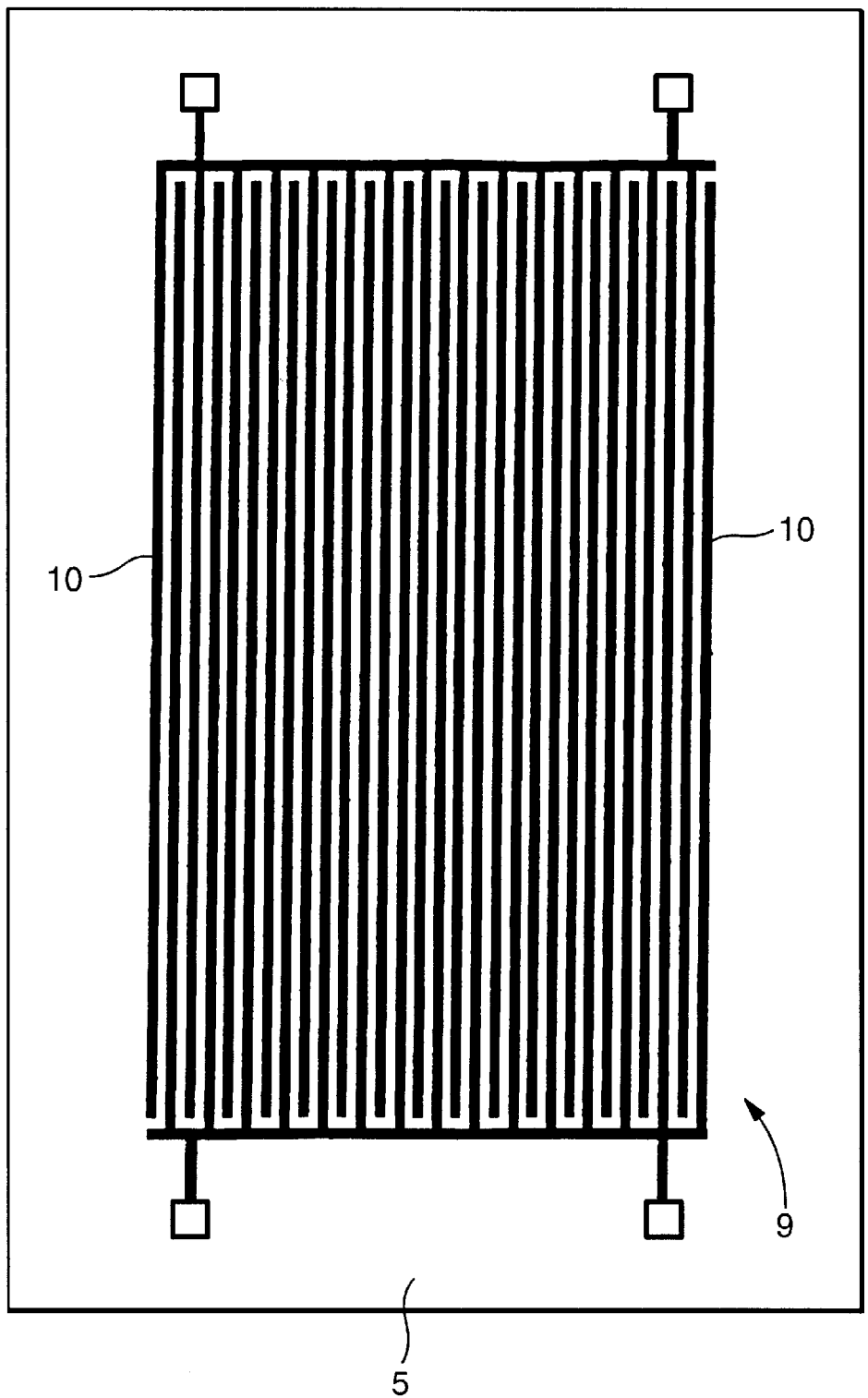
FIG. 2 is an interdigital capacitor which is situated on a substrate and has interleaving comb-type electrodes.
Figure 3:
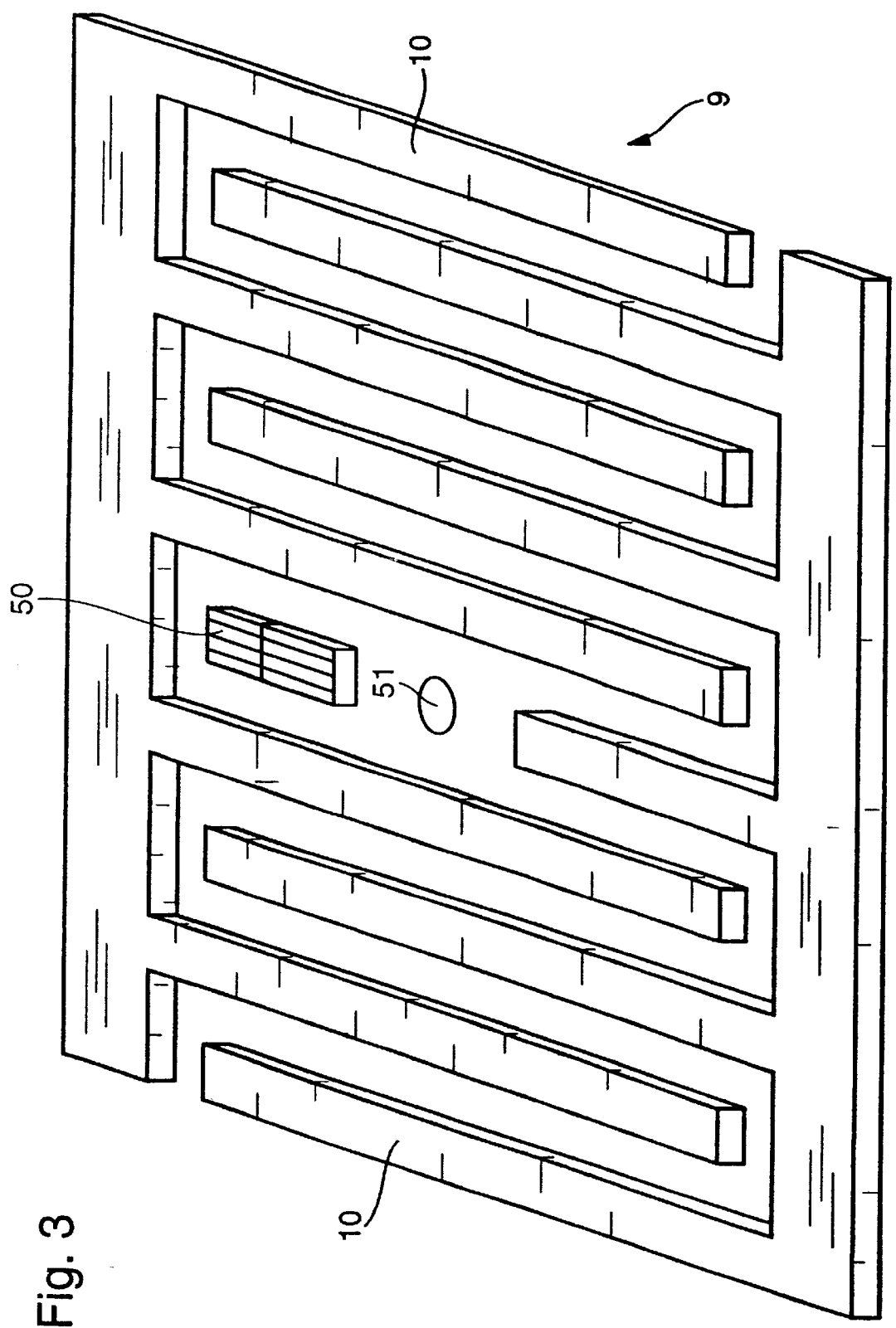
FIG. 3 is a three-dimensional representation of the electrodes of an interdigital capacitor.
Figure 4:
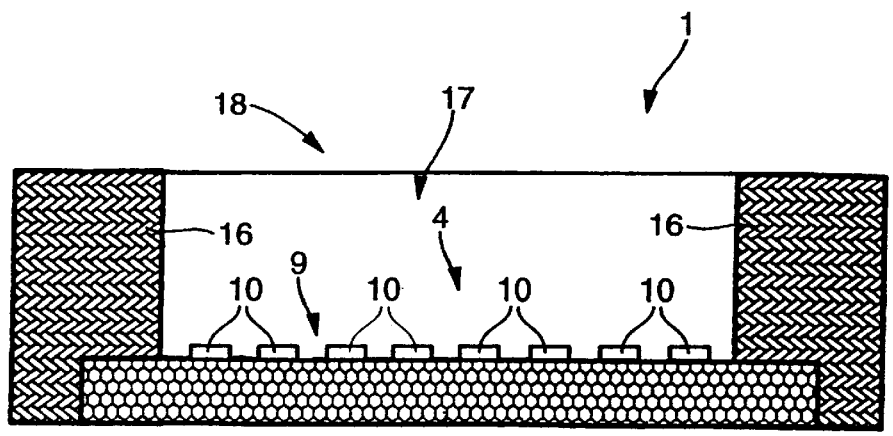
FIG. 4 is a cross section through the substrate without the receptor cells situated on it, whereby an interdigital capacitor is provided as measurement structure and whereby the receptacle bounding the measurement area is also to be seen.
Figure 5A:
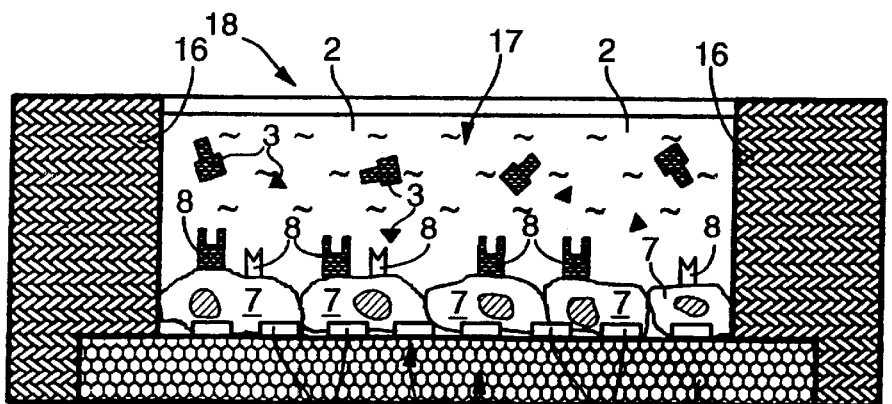
FIG. 5a is a representation similar to FIG. 4, however additionally showing the receptor cells directly attached to the measurement structure and the receptacle filled with analyte.
Figure 5B:
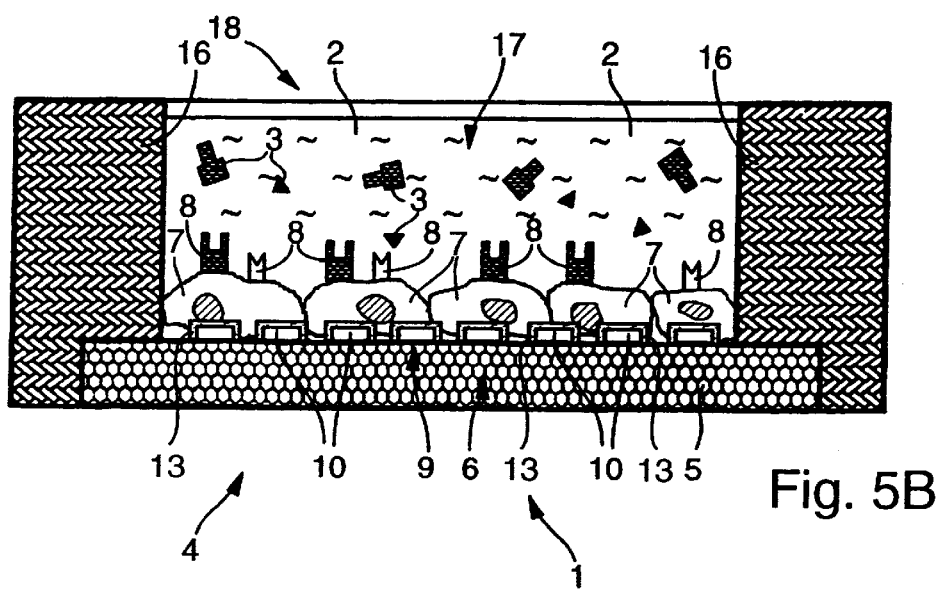
FIG. 5b shows the interdigital capacitor with the structured microporous interlayer.

In the embodiment shown in FIG. 5a, an interdigital capacitor 9 is provided as measurement structure 6. The electrodes 10 of the interdigital capacitor 9 are formed by mutually adjacent conductors arranged on a flat substrate 5 which may consist of e.g. glass, sapphire or silicon. FIG. 5b shows the interdigital capaciter (9) with the structured microporous interlayer (13). FIGS. 1 to 3 show exemplary embodiments of interdigital capacitors 9 with different electrode layout. In the example according to FIG. 1, the electrodes 10 are formed by two conductors extending in equidistant relationship, arranged in meanderform on the surface of the substrate 5. In another embodiment (FIGS. 2 and 3), the interdigital capacitor 9 has two interleaved comb-type electrodes. Using the interdigital capacitor 9, changes in shape of the target cells or receptor cells 7 as well as impedance changes at the cell membrane of these cells can be measured. Through its planar configuration, the interdigital capacitor 9 renders possible a measuring device 1 producible with especial cost advantage and in large volume. It is of particular advantage that the electrode structure of the interdigital capacitor 9 can also be applied to biocompatible substrates.

As shown in FIG. 3, light guides 51 are preferably provided in between the electrodes 10 of the interdigital capacitor 9. Light detectors, such as CCD sensors 50 in the form of a CCD line or CCD array, are provided for the reception and detection of the light passing through the respective light guides 51 and are arranged in the substrates.

As shown in FIG. 3, light guides 51 are preferably provided in between the electrodes 10 of the interdigital capacitor 9. Light detectors, such as CCD sensors 50 in the form of a CCD line or CCD array, are provided for the reception and detection of the light passing through the respective light guides 51 and are arranged in the substrate.

FIGS. 6 to 9 show exemplary embodiments of the measuring device 1, in which an ISFET 11 is provided as sensor, the gate 12 of which is exposed for contact with the receptor cells 7. Between that area of the ISFET 11 which is active for measurement and the receptor cells 7 is an interlayer 13 whose one face is in direct contact with the gate 12 and whose other face is in direct contact with the receptor cells 7. The interlayer 13 is a macromolecular porous layer which on the one hand renders the receptor cells 7 adherent and on the other hand is proportioned in its pore size so as to be permeable for certain ions, molecules or cell areas. The interlayer 13 is hence biocompatible, so that the receptor cells 7 accept it as neighbor and adhere to it. Nevertheless, measurement is not impeded by the interlayer 13 situated between the measurement structure 6 and the receptor cells 7, because the interlayer is permeable for the molecules, ions or cell areas to be detected.

Figure 9:
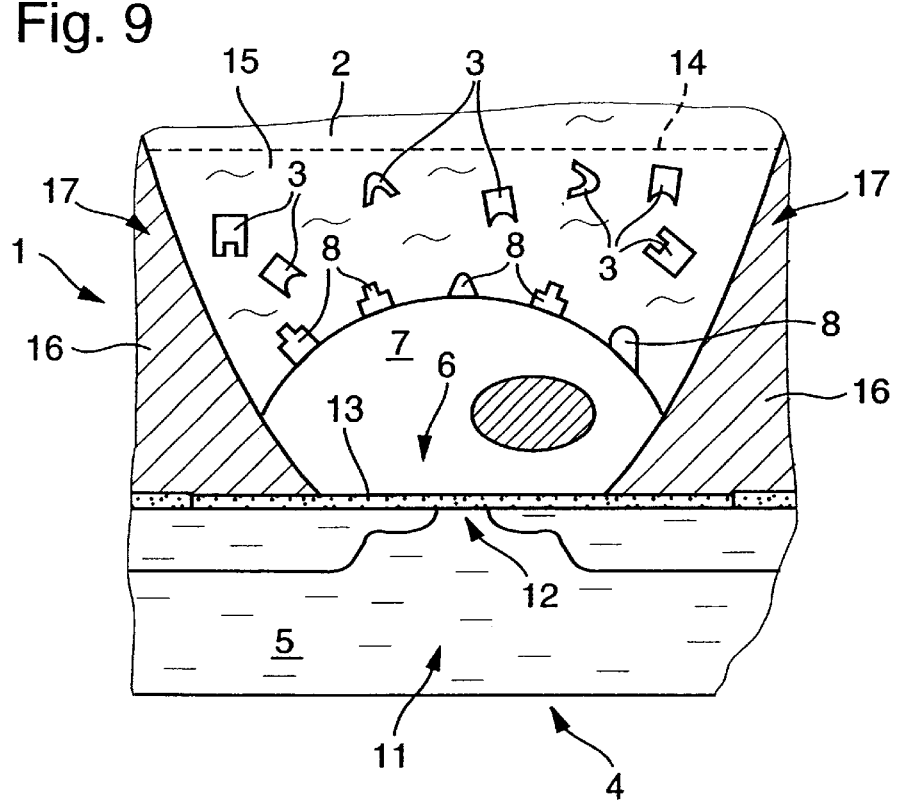
FIG. 9 is a representation similar to FIG. 8, however the receptor cell is arranged in a gel layer having a gel membrane.

In the exemplary embodiment shown in FIG. 9, the target cells or receptor cells 7 are arranged in a gel structure 15 having a membrane 14. The gel structure 15 contains a nutrient medium and therefore serves as a nutritional reservoir for the target cells or receptor cells 7. In addition, moisture is stored in the gel structure 15, so that the target cells or receptor cells 7 can be kept alive for a longer period. Therefore continuous online-analysis of certain components 3 contained in the analyte 2 is rendered possible by the measuring device 1, even over longer stretches of time. At the same time, the gel structure 15 and the membrane 14 are permeable for the components 3 to be detected, so that they can reach the receptors 8 of the receptor cells 7.

Figure 8:
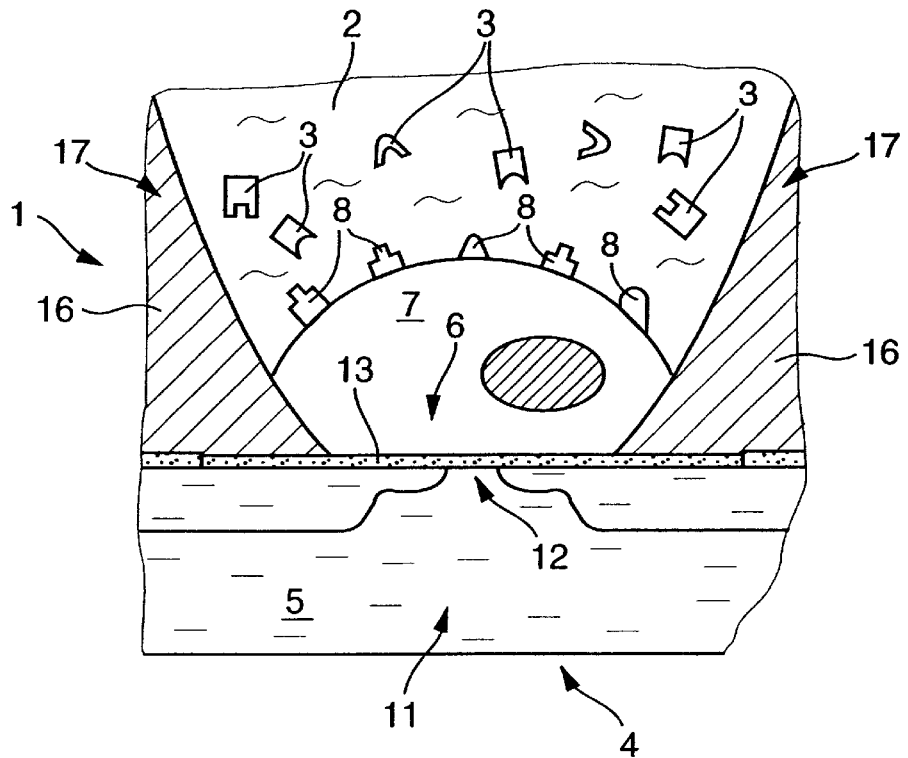
FIG. 8 is a partial view of the measuring device, showing an ISFET with an interlayer with which a receptor cell is in direct contact, the measuring area of the ISFET being laterally defined by a receptacle containing an analyte.

In the exemplary embodiment shown in FIG. 8, the nutrient medium for the receptor cells 7 is contained in the analyte 2, enabling on-line signal acquisition over a longer period in this instance as well.

As may be seen especially clearly in FIGS. 4, 5, 8 and 9, the measurement structure 6 is part of a wall 16 of a receptacle 17. The measurement structure 6 and the target cells or receptor cells 7 situated on it are arranged on the bottom of the receptacle 17, so that the analyte 2 can be filled into the receptacle 17 in a simple fashion and then immediately comes into contact with the target cells or receptor cells 7. The side walls 16 of the receptacle 17 are tightly connected to the substrate 5 and bound the area 6 designated for measurement. Even given a relatively large amount of a medium to be analyzed, it is thereby prevented from flowing out sidewards and, in so doing, from coming into contact with areas of the sensor 4 that are not intended for this, particularly with its connecting contacts.

Figure 6:
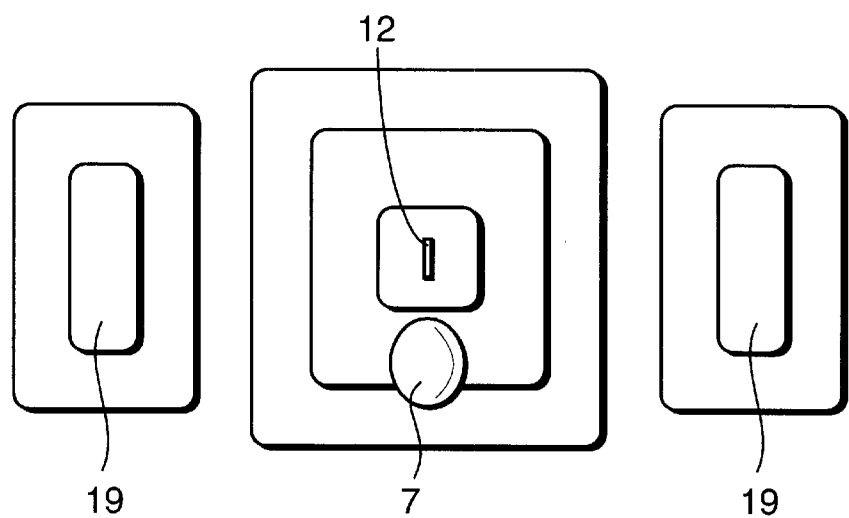
FIG. 6 is a plan view of the gate area of an ISFET with stimulating electrodes.
Figure 7:
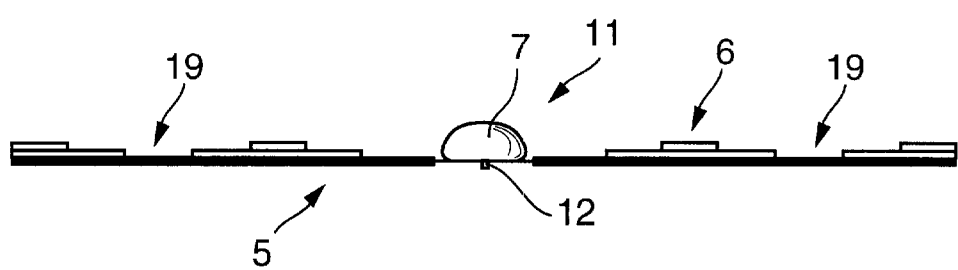
FIG. 7 is a cross section through the ISFET shown in FIG. 6, with a target cell situated on the gate.
Figure 10:
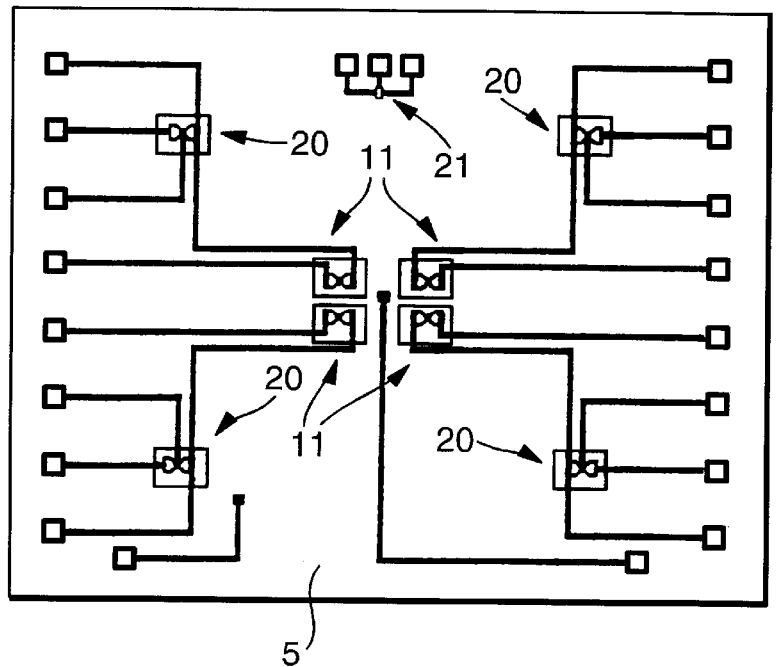
FIG. 10 is a plan view of a semiconductor substrate in which four ISFETS, four reference FETS and a temperature diode are integrated.
Figure 11:
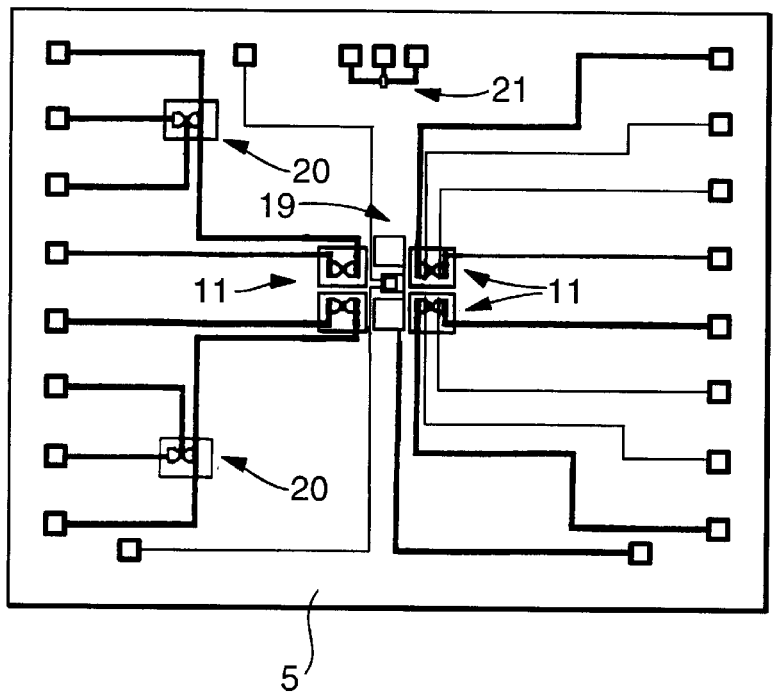
FIG. 11 is a plan view of a semiconductor substrate with four ISFETS between which a reference electrode is arranged, as well as with two reference FETS and a temperature diode.

In the case of the substrates 5 shown in FIGS. 6 and 7, provided at both sides of an ISFET 11 are stimulating electrodes 19, one at each, with which the receptor cells 7 can be induced to spontaneously release a substance to be detected. It is especially advantageous if a plurality of sensors 4 are arranged on a common substrate 5. FIGS. 10 and 11 show this, by way of example, with respect to a substrate 5 having four ISFETs designated for contact with target cells or receptor cells 7. In addition, four further ISFETs serving as reference elements 20 are integrated in the substrate 5, outside the substrate area designated for growth with the target cells or test cells. The reference elements or reference sensors 20 enable a compensation of the temperature drift and of the offset voltage of the sensors 4. In case of need, further stimulating electrodes 19 can be provided adjacent to the sensors 4 (FIG. 11).

Figure 12:
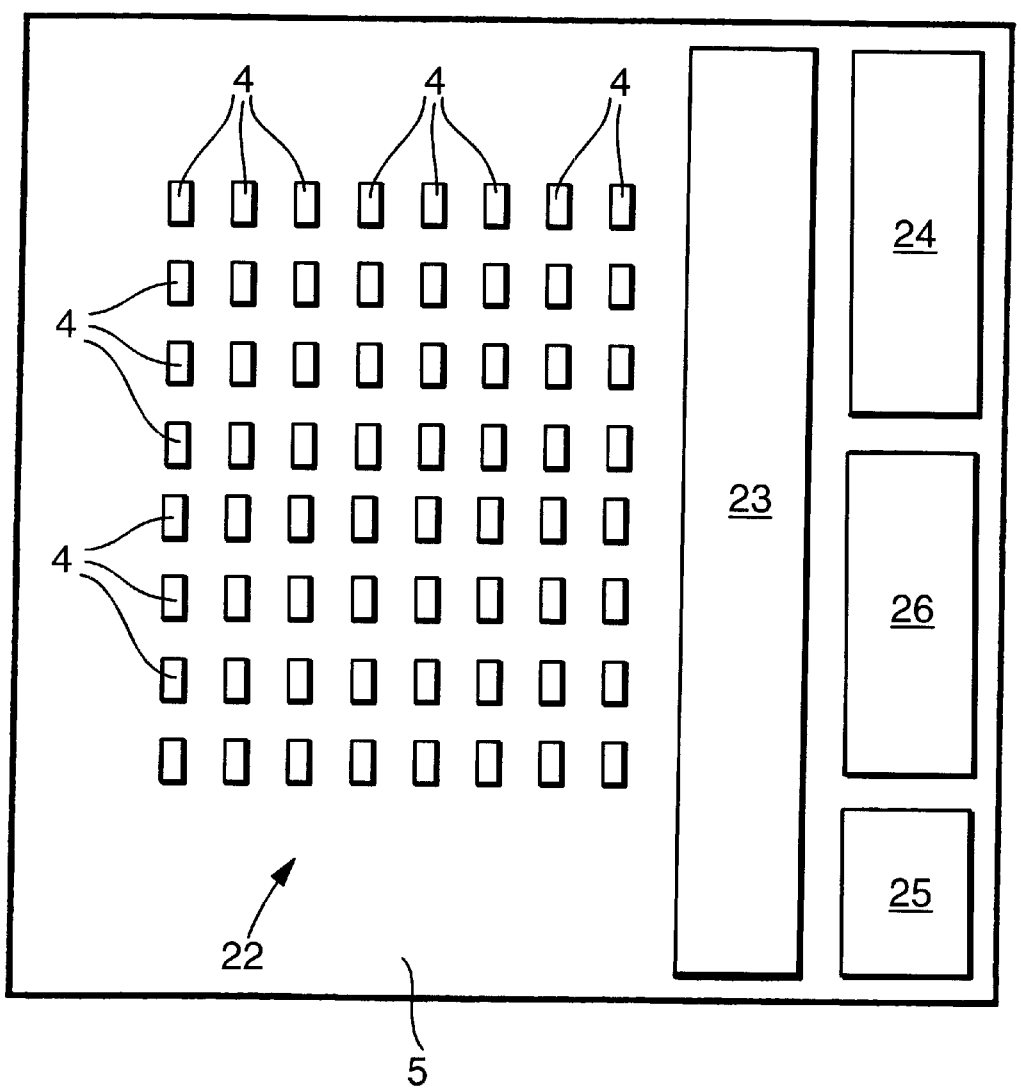
FIG. 12 is a plan view of a semiconductor substrate with a sensor array consisting of ISFETS and interdigital capacitors, whereby a microprocessor with AD/DA converter, multiplexer and IO unit are also provided on the semiconductor substrate.
Figure 13:
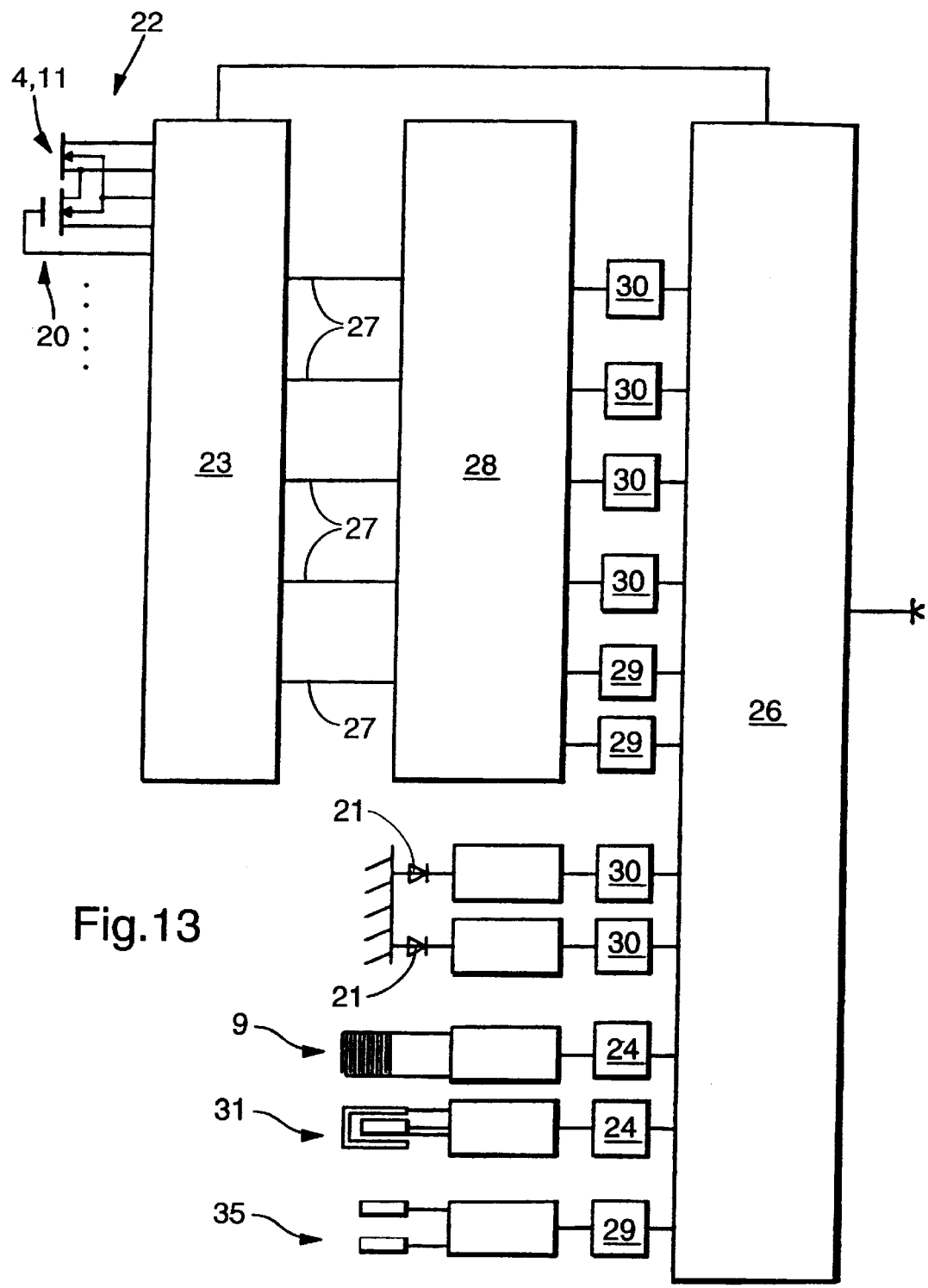
FIG. 13 is the block diagram of the biosensor chip shown in FIG. 12.
Figure 14:
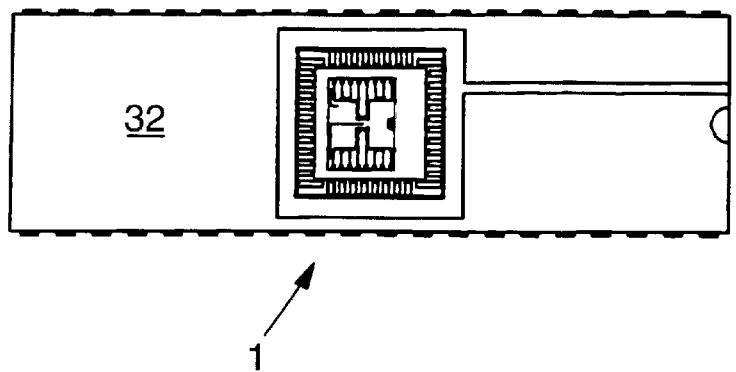
FIG. 14 is a plan view of a measuring device incorporated in a dual inline package.
Figure 15:
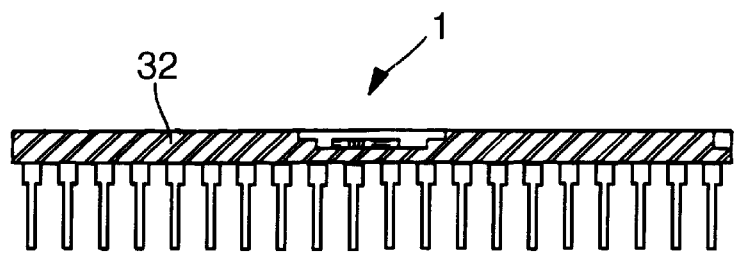
FIG. 15 is a section through the longitudinal center plane of the measuring device shown in FIG. 14.
Figure 16:
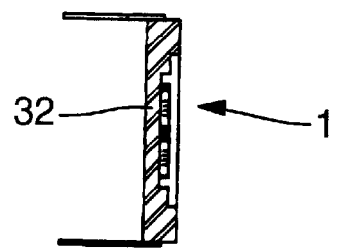
FIG. 16 is a section through the transverse center plane of the measuring device shown in FIG. 14.

It is especially advantageous if the sensors 4 are arranged in the form of an array on the substrate 5 (FIG. 12). Several different chemical or biological components 3 can then be concurrently detected using a single measuring device 1. In addition, there is the possibility of a parallel measurement signal acquisition at different target or receptor cells, allowing a check on the measurement results. In the exemplary embodiment shown in FIG. 12, in addition to the sensor array 22, also integrated are a multiplexer 23, an AD/DA conversion unit 24, an IO unit 25 and a microprocessor 26. As may be noted from the accompanying block diagram (FIG. 13), in each case one of five simultaneously selectable measuring circuits 27 can be assigned to optional sensors arranged on the substrate 5. A control unit 28 allows an adjustment of the current and voltage values envisaged for the selected sensors 4 and for the reference elements 20 assigned to them. The corresponding values are determined by the microprocessor 26 and output to the control unit 28 via digital/analog converter 29. Analog/digital converters 30 are provided for reading in the measured values from the control unit 28. Also connected to the microprocessor are two temperature sensors 21, an interdigital capacitor 9, an oxygen sensor 31 and two AgCl reference electrodes 35.

The complete substrate 5 with the target cells or receptor cells 7 situated on it is incorporated in a 40-pin ceramic dual in-line header 32. By this means, like a commercially available integrated circuit, the measuring device 1 can be used for instance in an IC header provided on a board.

Figure 17:
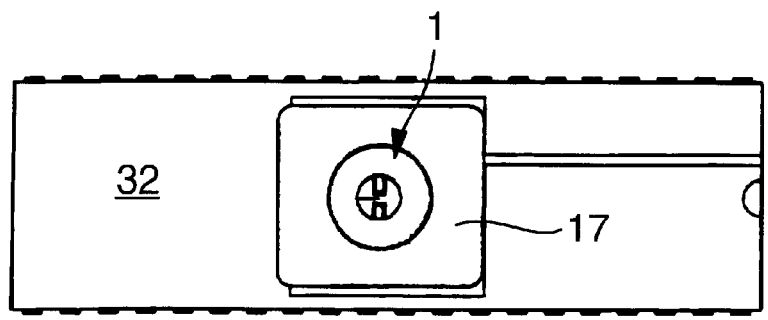
FIG. 17 is a plan view of a measuring device incorporated in a dual inline package with a receptacle for the analyte.
Figure 18:
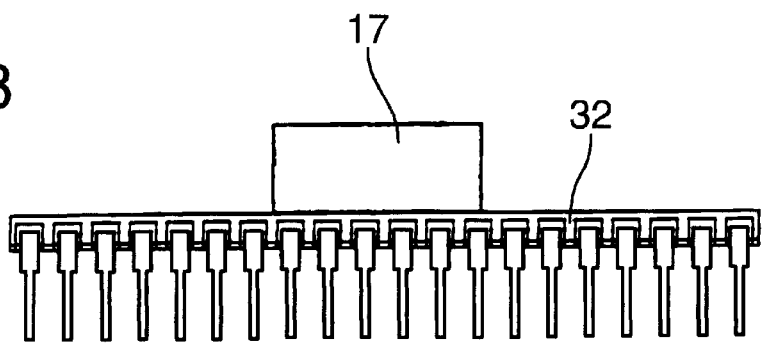
FIG. 18 is a view of the long side of the measuring device shown in FIG. 17, showing the receptacle and the connection contacts of the dual in-line package especially clearly.
Figure 19:
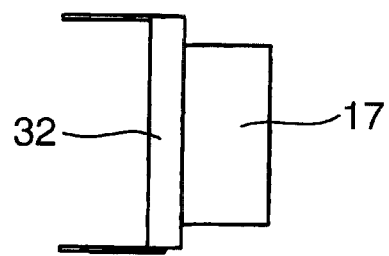
FIG. 19 is a side view of the narrow side of the measuring device shown in FIGS. 17 and 18.
Figure 20:
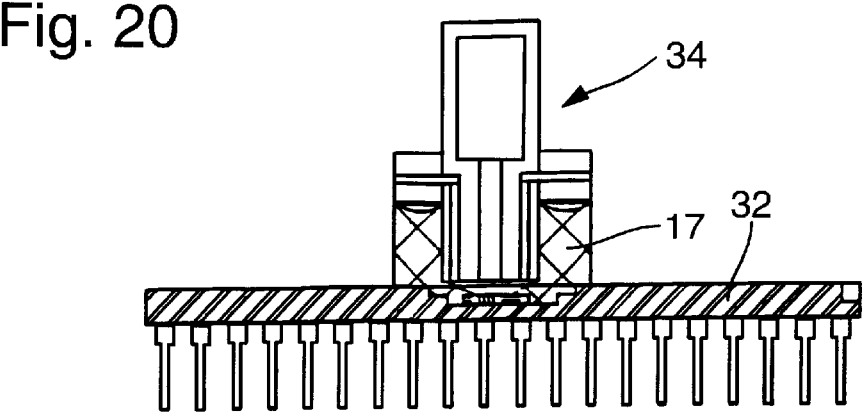
FIG. 20 is a section through the longitudinal center plane of a measuring device similar to that in FIG. 17, however a flow attachment with integrated reference electrode is placed on the filler inlet of the receptacle.
Figure 21:
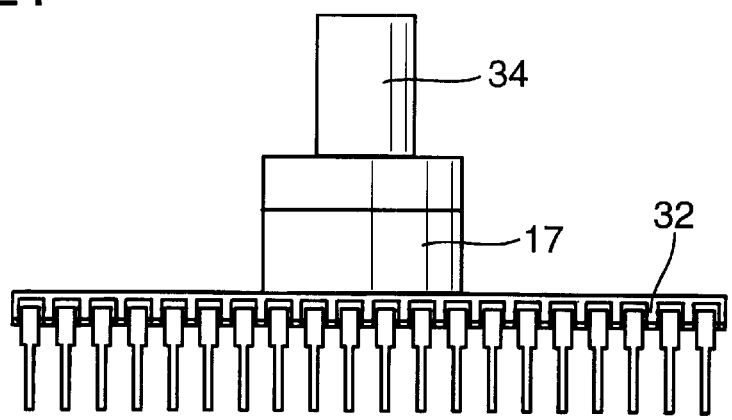
FIG. 21 is a view of the long side of the measuring device shown in FIG. 20.
Figure 22:
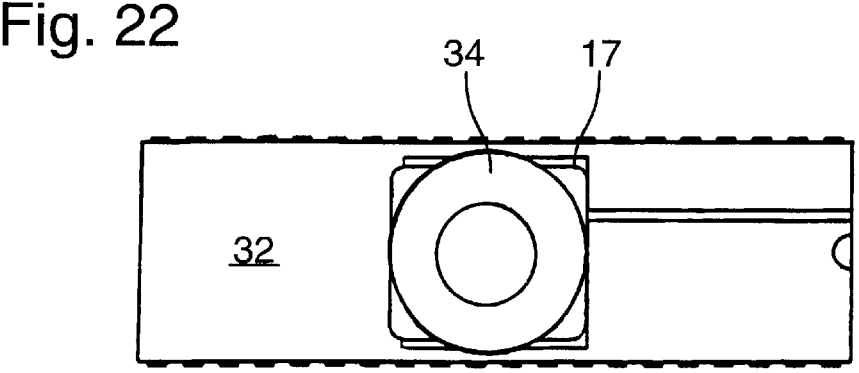
FIG. 22 is a plan view of the measuring device shown in FIG. 20.

FIGS. 17 to 19 show exemplary embodiments in which a receptacle 17 for the analyte 2 is provided on the ceramic dual in-line header 32. The analyte 2 can then be filled into the receptacle 17 in a simple fashion. To enable particularly exact positioning of the analyte 2 in relation to the sensors 4, a flow attachment 34 can be placed in the filler inlet 18 of the receptacle 17. Diffusion differences of the analyte 2, as may occur in the region of the sensor 4 when filling or sucking off the analyte with a pipette, are thereby largely avoided.

What is claimed is:

1. A measuring device (1) for measuring the presence of at least one component (3) contained in an analyte (2), said device comprising a plurality of sensors including at least one reference sensor and at least one electrical sensor (4) each having a measurement output connectable to an evaluating device, wherein the electrical sensor (4) and the reference sensor each have an electrical measurement structure (6) located on a common substrate (5), the measurement structure (6) of the electrical sensor is connected to at least one function-specific plant or animal receptor cell (7) serving as a biological sensor, wherein each electrical sensor measures the analyte (2) under investigation by measuring a morphologic or physiologic property of the receptor cell (7), wherein provided between the receptor cell and the measurement structure (6) is a structured, biocompatible micro porous interlayer (13) to which the receptor cell at least partially adheres, the measurement structure of the reference sensor being free of connections to function-specific receptor cells (7), the reference sensor and the at least one electrical sensor being arranged on the common substrate (5) to form a sensor array (22), whereby a change of the property is indicative of the presence of the component in the analyte.

2. A measuring device as claimed in claim 1, wherein the measurement outputs of the sensors (4) arranged on a common substrate (5) are connected to a control and evaluating device that is integrated on the common substrate (5).

3. A measuring device as claimed in claim 2, wherein on the substrate (5) with the sensor array (22) are a multiplexer (23), an AD/DA converter (24) with sensor control, a microprocessor (26) and an IO unit (25) as a control and evaluating device.

4. A measuring device as claimed in claim 1, wherein at least one stimulating electrode (19) for the receptor cell is arranged on the substrate (5) within or adjacent to a measurement area of a corresponding measurement structure (6).

5. A measuring device as claimed in claim 1, wherein the substrate (5) is a semiconductor substrate and wherein the measurement structure is provided in the form of at least one ISFET (11) whose gate (12) is adjacent to the interlayer (13) opposite from the receptor cell (7).

6. A measuring device as claimed in claim 1, wherein the measurement structure (6) is provided in the form of at least one interdigital capacitor (9) exhibiting electrodes (10) that are interleaved in pairs.

7. A measuring device as claimed in claim 6, wherein a plurality of interdigital capacitors (9) varying in size are provided.

8. A measuring device as claimed in claim 6, wherein the plurality of sensors that are reactive to at least one component that the analyte is being investigated for is provided in at least one insulated interspace of the electrodes (10) of the interdigital capacitor (9).

9. A measuring device as claimed in claim 6, wherein light guides are provided between the electrodes (10) of the interdigital capacitor (9) and that light detectors for the reception and detection of the light passing through the respective light guide are arranged in the substrate (5).

10. A measuring device as claimed in claim 1, wherein CCD sensors, in particular in the form of a CCD line or CCD array, are integrated in the substrate (5).

11. A measuring device as claimed in claim 1, wherein the at least one reference sensor (20) comprises a field effect transistor disposed on the substrate (5) outside a substrate area designated for the measurement.

12. A measuring device as claimed in claim 1, wherein at least one temperature measuring diode is arranged on the substrate (5) supporting the measurement structure (6).

13. A measuring device as claimed in claim 1, wherein the receptor cells (7) are arranged in a gel structure (15) that is permeable to the specific component being tested for and that provides a nutritional reservoir for the receptor cell (7).

14. A measuring device as claimed in claim 1, wherein the electrical measurement structure (6) is part of a wall (16) of a receptacle (17) for the analyte.

15. A measuring device as claimed in claim 14, wherein the measurement structure (6) is situated on the bottom of the receptacle (17) and that a plurality of side walls are formed by an encapsulation bounding a measurement area of the measurement structure (6).

16. A measuring device as claimed in any one of claims 1 to 19, wherein a plurality of measurement structures (6) are arranged side by side.

17. A measuring device as claimed in claim 1, wherein the electrical contact points and/or the structured biocompatible interlayers (13) of at least two measurement structures (6) have different electrical properties.

* * * * *